(12) United States Patent
Takahama et al.

(10) Patent No.: US 6,342,767 B2
(45) Date of Patent: Jan. 29, 2002

(54) MOBILE TYPE X-RAY APPARATUS

(75) Inventors: Kimihiro Takahama; Toshio Kadowaki, both of Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/759,518

(22) Filed: Jan. 16, 2001

(30) Foreign Application Priority Data

Jan. 31, 2000 (JP) ........................................ 2000-022578

(51) Int. Cl.[7] ............................................... H02K 33/00
(52) U.S. Cl. ............................. 318/37; 53/115; 180/411
(58) Field of Search ............................. 318/34, 35, 37, 318/38, 45, 47, 53, 59, 60, 61, 64, 66, 115, 159, 160, 830, 831, 489, 552–557; 180/409, 411, 412, 413; 378/193, 197, 198

(56) References Cited

U.S. PATENT DOCUMENTS 4,556,940 A * 12/1985 Katoo et al. ................. 318/552
6,131,690 A * 10/2000 Galando et al. ............. 180/411

* cited by examiner

Primary Examiner—Khanh Dang
(74) Attorney, Agent, or Firm—Kanesaka & Takeuchi

(57) ABSTRACT

In a mobile type X-ray apparatus, an input shaft of a cyclo-decelerator is connected to one end of a rotational shaft of a motor, and the other end of the rotational shaft is connected to an encoder and an electromagnetic brake. The cyclo-decelerator is attached to a frame. Also, a bearing is fitted in the frame, and a wheel hub is fitted between the bearing and a motor output shaft. A wheel is fixed to the wheel hub. By the cyclo-decelerating mechanism, a transmission of power is carried out among contact surfaces of an eccentric cam, epitrochoid teeth and rollers, so that the apparatus has a compact structure with a low noise and no backlash.

2 Claims, 5 Drawing Sheets

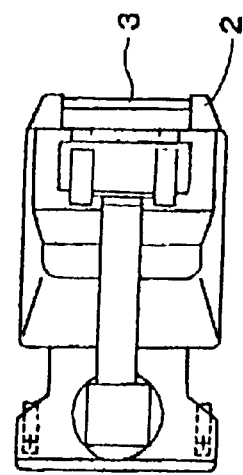
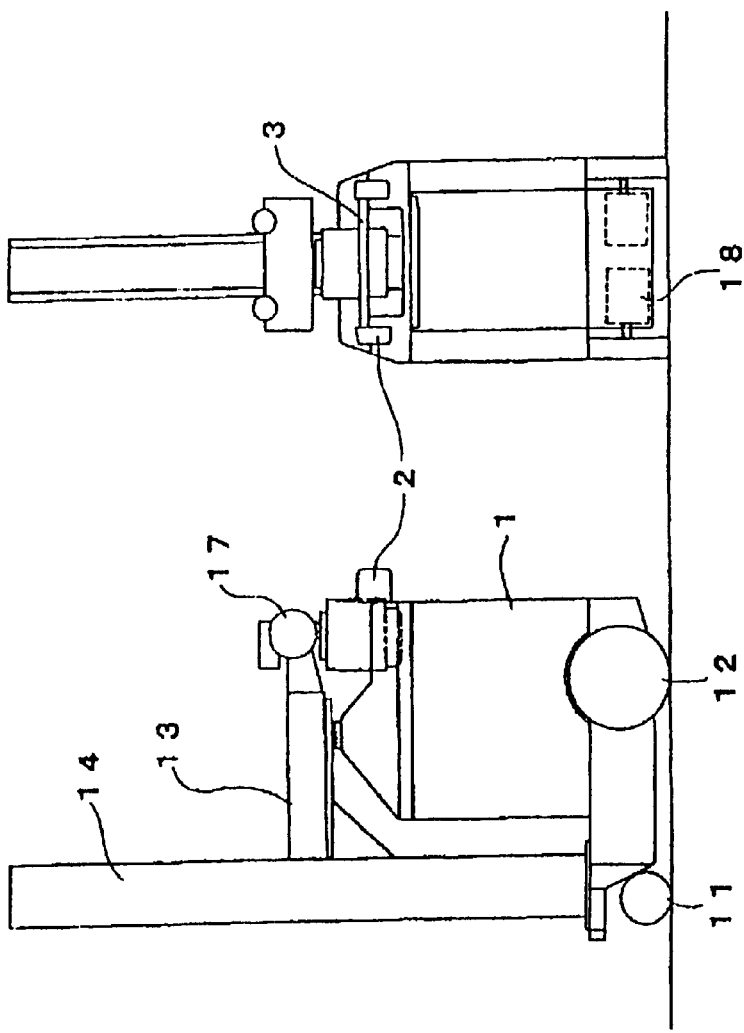
Fig. 3(a) Prior Art
Fig. 3(b) Prior Art
Fig. 3(c) Prior Art

MOBILE TYPE X-RAY APPARATUS

BACKGROUND OF THE INVENTION AND RELATED ART STATEMENT

The present invention relates to a mobile type X-ray apparatus, and more particularly, to an X-ray apparatus which includes a power driving type truck moving forward or backward in response to a force of an operation handle.

FIGS. 3(a) through 3(c) show a conventional mobile type X-ray apparatus or X-ray photographing apparatus with a cordless inverter system for a circuit examination by a doctor. FIG. 3(a) shows a front view; FIG. 3(b) shows a side view; and FIG. 3(c) shows a plan view thereof. The X-ray photographing apparatus includes an X-ray tube 17; an arm 13 for supporting the X-ray tube 17; a column 14 freely rotatable on a truck or main body 1; and an ascending and descending section, in which the arm 13 moves vertically or up and down along the column 14. The truck 1 is provided with freely pivotable front wheels 11 and rear wheels 12 incapable of steering. The truck 1 also includes a controller, and is moved forward or backward by driving motors 18 by operation of an operation handle 3 forwardly or backwardly, which is provided at handle supporting bases 2 attached to the truck 1.

The arm 13, which includes a supporting mechanism for the X-ray tube 17 and a rotating mechanism therefor, and extends or retracts in a horizontal direction, is designed to move vertically along the column 14 smoothly so as to be balanced. In the apparatus, a collimator (X-ray radiation port) of the X-ray tube 17 is directed to portions of a subject to be photographed, i.e. a person to be examined, from all the directions in all spatial positions.

Since the weight of the movable type X-ray photographing apparatus may become more than 450 kg, it is extremely difficult to move the truck without a help of the power. Generally, a pair of the rear wheels 12, which are fixed not to change directions, is provided at a rear portion of the truck 1, and a front portion of the truck 1 is supported by a pair of casters, that is, freely pivotable from wheels 11. The rear wheels 12 are generally driven by the driving motors 18 attached to the truck.

The truck 1 includes an internal power supply with a main circuit of 100 to 120 V and 60 Hz, which is formed of a battery and an inverter, and the truck 1 also includes a high-voltage transformer and an inverter control device. In many cases, there is used an apparatus of a one-touch system, wherein a control circuit thereof is systematized and a photographing operation is automatically programmed.

Also, the truck 1 is designed to have rubber tires such that the truck 1 can freely enter or leave a patient's room, an operating room, and an elevator, and the truck 1 is further provided with a brake system, a cassette box, and accessories.

It is important that the movable X-ray photographing apparatus is small, light-weighted, and excellent in a moving operation ability as a mobile type apparatus, and the movable X-ray photographing apparatus is easily moved to a bedroom, an operating room, a children room or a pediatric room, an X-ray room, an infant room or the like in a hospital, and conveniently used for an X-ray photographing or radiography at a working site, that is, the location where the apparatus is moved.

FIG. 4 shows a diagram of a control system of the conventional mobile type X-ray apparatus. The truck or frame 1 is shown at an upper side in FIG. 4, and a left rear wheel 12a and a right rear wheel 12b are respectively driven by a left driving motor 18a and a right driving motor 18b. The left driving motor 18a and the right driving motor 18b are individually controlled by a control board 19. In the control board 19, control signals are supplied from a corresponding left side sensor signal processing circuit and a corresponding right side sensor signal processing circuit. These two electronic circuits adjust signals, which are issued from a left advancing pressure sensor 6af, a left retreating pressure sensor 6ab, a right advancing pressure sensor 6bf, and a right retreating pressure sensor 6bb due to corresponding forces, to signals appropriate for applying to the Left driving motor 18a and right driving motor 18b. T hen, rotational speeds from the left driving motor 18a and the right driving motor 18bare respectively detected by a left pulse encoder 19a and a right pulse encoder 19b, and signals thereof are fed back to the control board 19, so that the control is carried out to have appropriate driving speeds.

In this electrically powered mobile type X-ray apparatus, a power from an output shaft of a rotor in the driving motor 18 is transmitted to the rear wheel 12 through a decelerating mechanism. As the decelerating mechanism, there are a mechanism wherein a planetary gear type decelerator is embedded in the driving motor 18, and a mechanism wherein a planetary gear decelerating mechanism is built inside the rear wheel 12.

FIG. 5 shows a planetary gear mechanism. The planetary gear mechanism is a mechanism such that in a pair of gears engaging each other (sun gear 4 and planetary gear 5), the two gears respectively rotate on their own axes, and at the same time, one of the gears (planetary gear 5) revolves around the axis of the other gear (sun gear 4). The gear, which not only rotates on its own axis but also revolves at the revolving axis, constitutes the planetary gear 5; the gear, wherein a position of the axis thereof does not change, constitutes the sun gear 4; and a member for supporting the planetary gear 5 constitutes a carrier 8. One of an internal gear 7, the sun gear 4 and the carrier 8, which are provided coaxially, is fixed, and the other two are used as input and output axes to have functions of deceleration, acceleration, and reversing.

The conventional mobile type X-ray apparatus is structured as described above. However, in the apparatus, wherein the planetary gear type decelerator is embedded as the decelerator in the driving motor 18, in order to transmit the power from the output shaft of the rotor inside the driving motor 18 to the rear wheel 12, according to the structure thereof, a gear sound of meshing the gears is generated, resulting in a problem in case the apparatus is moving in a quiet place inside the hospital.

Also, in the apparatus in which the planetary gear type decelerator is embedded, since a backlash is large, an operator can not control the apparatus desirably, resulting in a problem that a positioning of the apparatus at a bed side in a narrow patient's room is difficult.

On the other hand, in case the decelerating mechanism is built in the rear wheel 12, it is necessary to transmit the power by a belt between the driving motor 18 and the rear wheel 12, so that an occupied volume of the driving section is increased.

The present invention has been made in view of the foregoing, and an object of the invention is to provide a mobile type X-ray apparatus, which includes a compact decelerating mechanism and can be moved in a quiet condition, that it, in the condition that the gear sound of meshing the gears is not generated.

Another object of the invention is to provide a mobile type X-ray apparatus as described above, which can be easily operated by an operator, in other word, which has no difficulty in operation due to the backlash as in the conventional apparatus.

Further objects and advantages of the invention will be apparent from the following description of the invention.

SUMMARY OF THE INVENTION

To achieve the above objects, the present invention provides a mobile type X-ray apparatus, which comprises a pair of right and left driving motors; a pair of cyclo-decelerating mechanisms respectively built in the driving motors; and a pair of driving wheels respectively attached to the cyclo-decelerating mechanisms. The driving wheels are individually driven by the respective motors through the respective cyclo-decelerating mechanisms in response to an operation power in a direction applied to an operation handle.

The mobile type X-ray apparatus is structured as described above, and in order to transmit the power of the driving motor to the wheel, the cyclo-decelerating mechanism is provided inside the driving motor and connected to the axis of the wheel. Thus, the power is transmitted by an eccentric wheel and rollers in the cyclo-decelerating mechanism, so that the apparatus can be moved quietly without making a noise. Also, since the backlash is small, the operation ability of the apparatus is improved. Further, since the cyclo-decelerating mechanism is built in the driving motor and connected to the axis of the wheel, the apparatus can be structured to be compact.

BRIEF DESCRIPTION OF THE DRAWINGS

FIGS. 3(a) through 3(c) are views for showing an appearance of a conventional mobile type X-ray apparatus;

DETAILED DESCRIPTION OF PREFERRED EMBODIMENT

Figure 1:
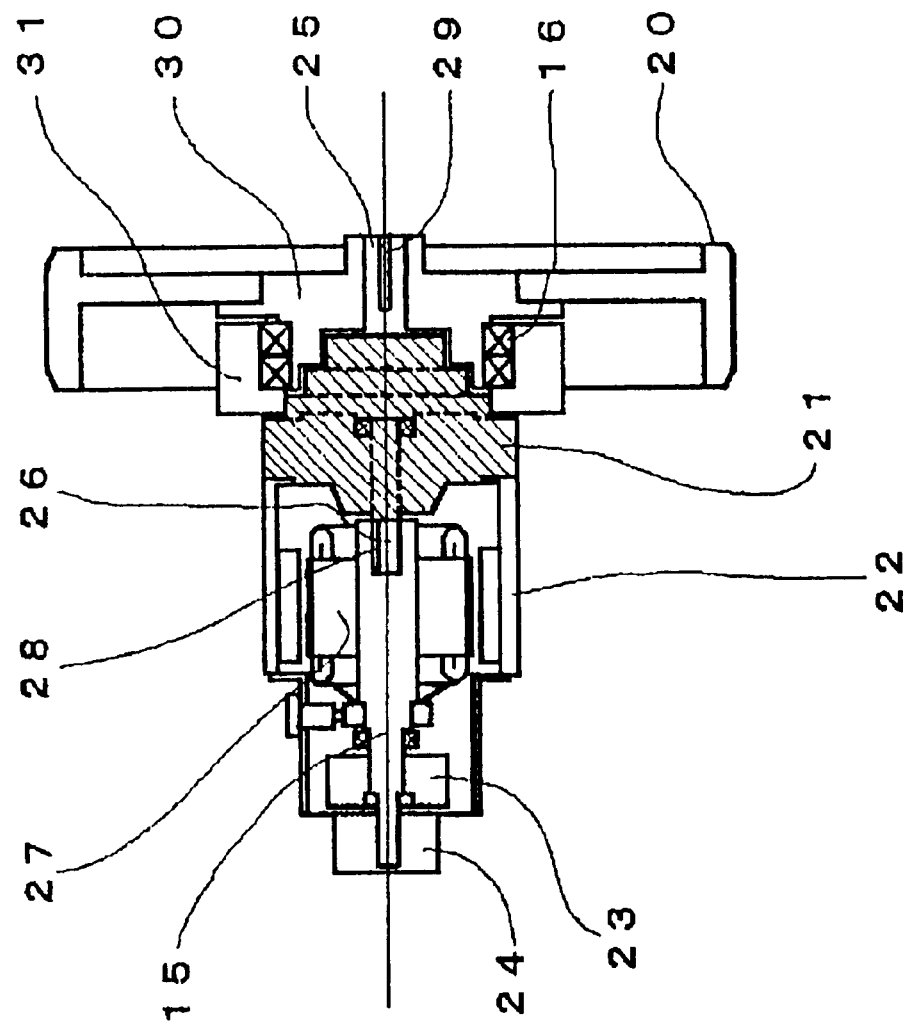
FIG. 1 is a sectional view of an embodiment of a decelerating mechanism for a mobile type X-ray apparatus of the invention.

An embodiment of the mobile type X-ray apparatus of the invention will be explained with reference to FIG. 1. FIG. 1 shows a sectional view of a part wherein a driving motor, a cyclo-decelerator, and a wheel of the mobile type X-ray apparatus of the invention are connected.

The apparatus is formed of a motor main body 22 including a rotor 27; a cyclo-decelerator 21 which is connected to a rotational shaft 15 of the motor main body 22 through a key 28 and fixed to a truck frame 31; a wheel or wheel hub 30 which is connected to a motor output shaft 25 of the cyclo-decelerator 21 through a key 29 and attached to the truck frame 31 through a bearing 16; a wheel 20 fixed to the wheel hub 30; an encoder 23 which detects a rotational speed of the driving motor; and an electromagnetic brake 24 which applies a brake on the rotational shaft 15.

Assembly of the motor main body 22, the cyclo-decelerator 21, and the wheel 20 is carried out in the following order. First, the encoder 23 and the electromagnetic brake 24 are attached to one end portion of the rotational shaft 15 of the motor main body 22, and the other end portion of the rotational shaft 15 of the motor main body 22 and an input shaft 26 of the cyclo-decelerator 21 are connected by the key 28, so that the rotational shaft 15 of the motor main body 22 and the input shaft 26 of the cyclo-decelerator 21 are coupled. Then, an exterior cover portion of the motor main body 22 is placed to cover the same. Next, an output side of the cyclo-decelerator 21 is fixed to the truck frame 31. Then, the bearing 16 is fitted with the wheel hub 30 to form a unit, and a bearing 16 side of the unit is fitted in the truck frame 31. At the same time, the key 29 is aligned with the motor output shaft 25 to be attached thereto, so that the motor output shaft 25 and the wheel hub 30 are fixed by the key 29. Then, the wheel 20 is fixed to the wheel hub 30 by a bolt.

Figure 4:
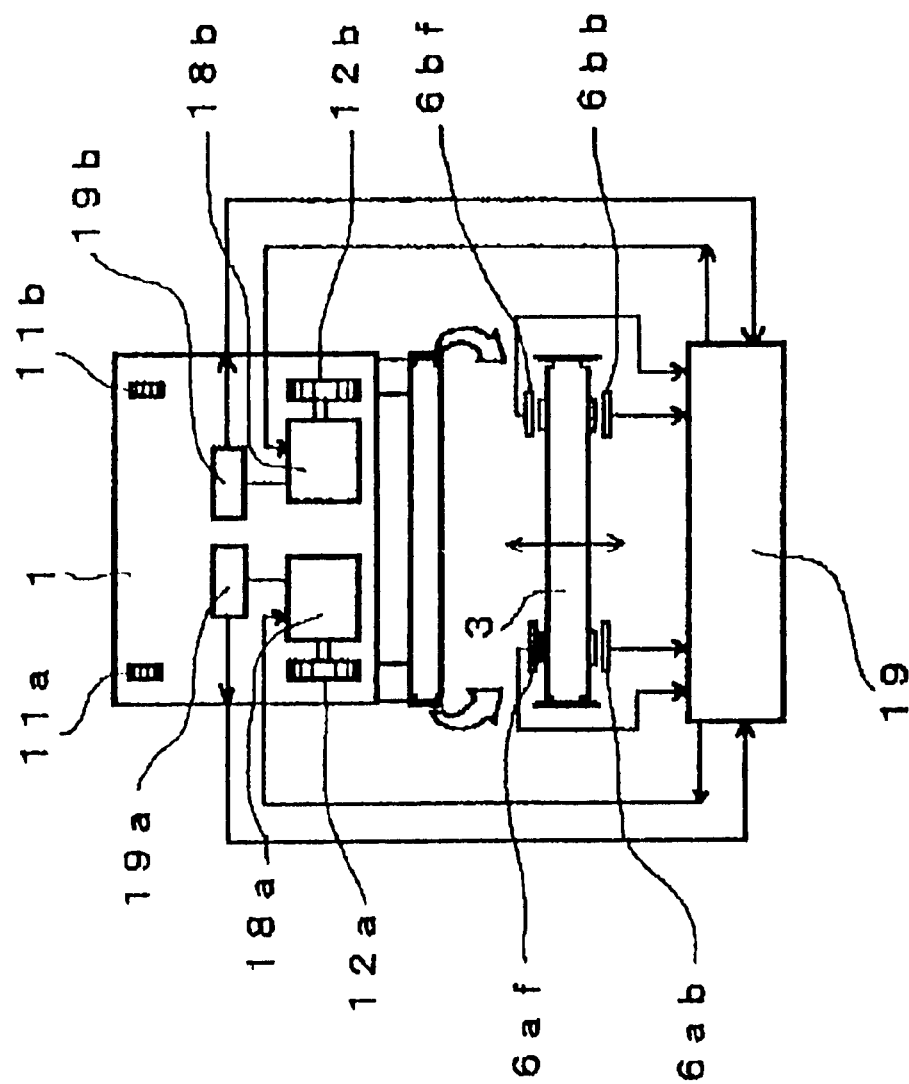
FIG. 4 is a diagram for showing a control system of a conventional mobile type X-ray apparatus.
Figure 5:
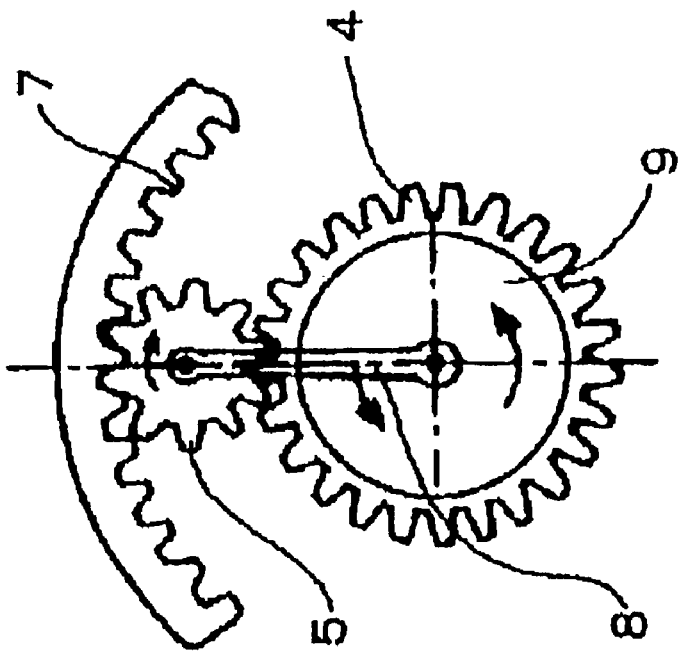
FIG. 5 is a view for explaining a conventional planetary gear decelerating mechanism.

Accordingly, the rotational speed of the rotational shaft 15 of the motor main body 22 is detected by the encoder 23, a feedback signal is sent from the control board 19 of the controller in the truck 1 shown in FIG. 4 to the motor main body 22 to rotate the motor main body 22, and a rotational power of the motor main body 22 is inputted into the cyclo-decelerator 21. Then, the rotational speed is reduced to a predetermined rotational speed, and the wheel 20 attached to the wheel hub 30 is rotated. Also, if necessary, the electromagnetic brake 24 is operated to brake the rotational shaft 15.

Figure 2:
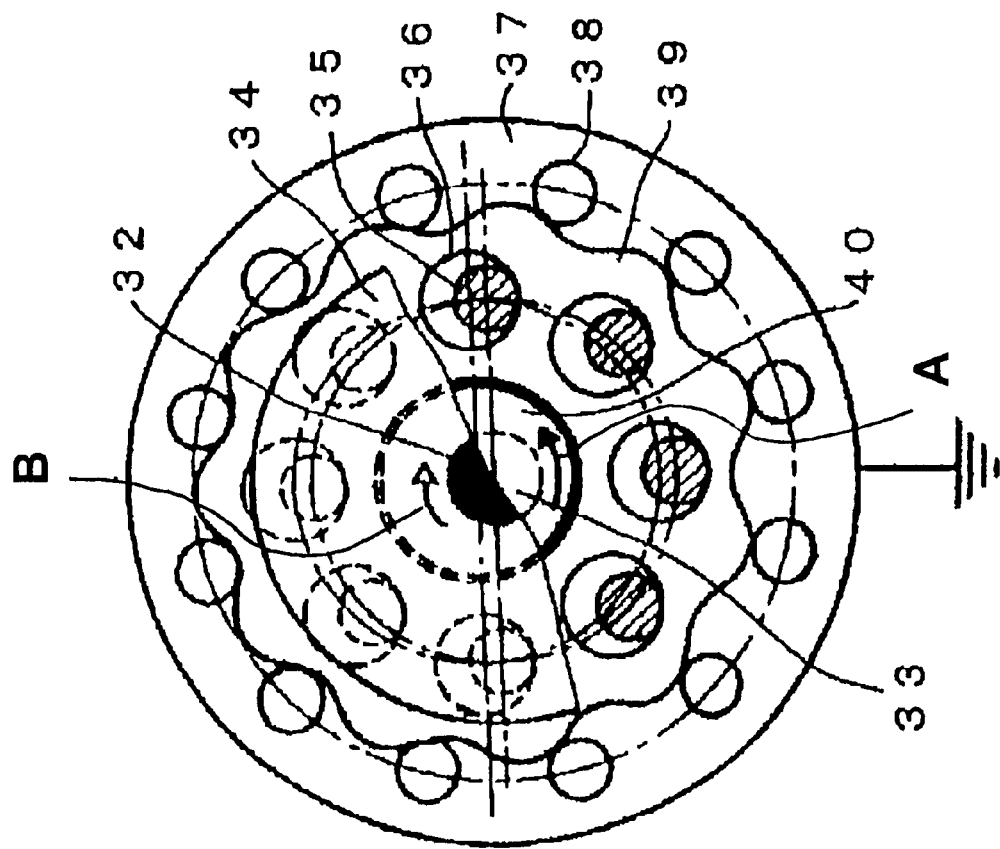
FIG. 2 is a view for explaining a cyclo-decelerator.

FIG. 2 shows a structure of the cyclo-decelerator 21 in an axial direction thereof. In the cyclo-decelerator 21, when an eccentric planetary gear 39, in which a form of epitrochoid teeth is employed, is rotated by an eccentric wheel 40 (eccentric cam) attached to a driving shaft 33 in a direction of a black arrow A, that is, in a counterclockwise direction in FIG. 2, the eccentric planetary gear 39 engages stationary pin gears 38 arranged on a circumference of a stationary disc 37, to thereby make a planetary movement. The movement of the eccentric planetary gear 39 on its own axis is taken out as an output rotation by means of rollers 35 fitting in or engaging with hole surfaces 36 of plural holes formed in the eccentric planetary gear 39. The rollers 35 are attached to a disc 34, and an output shaft 32 is fixed to a center of the disc 34, so that the disc 34 is rotated in a direction of an outlined arrow B, that is, in a clockwise direction in FIG. 2. The cyclo-decelerator described above is a kind of the planetary gear decelerator.

In the driving shaft 33 which rotates in the direction of the black arrow A, in other words, in the eccentric wheel 40, since the gear 39 fitted with the eccentric wheel 40 is engaged with the stationary pin gears 38 which are fixed, owing to a differential rotation, the gear 39 can obtain the rotational frequency or speed determined by {(size of the circumference to which the stationary pin gears 38 are fixed—size of the gear 39) × rotational frequency of the driving shaft 33/size of the gear 39}. Since the gear 39 is eccentric, by the engagement between the hole surfaces 36 and the rollers 35, the disc 34 concentric with the driving shaft 33 and attached with the rollers 35, in other words, the output shaft 32, is rotated in the direction of the outlined arrow B for reducing a speed.

In the cyclo-decelerator 21, a surface of the eccentric wheel 40, which is fixed to the driving shaft 33 as described above, and a surface of the planetary gear 39 are engaged with or rubbed against each other, and external epitrochoid teeth surfaces of the planetary gear 39 are engaged with surfaces of the stationary pin gears 38, so as to differentially rotate. The hole surfaces 36 of the planetary gear 39 engage the surfaces of the rollers 35 provided on the disc 34, so that the output shaft 32 attached to the disc 34 rotates for deceleration. Since the power is transmitted between the surfaces of the respective gears as described above, a noise is extremely small, and the backlash is decreased.

In the cyclo-decelerator, since the gear sound of meshing of the gears is very small as compared with that of the conventional planetary gear type decelerator, by building the decelerating mechanism into the driving motor, it is possible to operate with a low noise. Also, from the viewpoint of the structure, there is almost no backlash, so that the wheels 20 can be rotated as programmed in response to the input of the operation handle.

The mobile type X-ray apparatus of the invention is structured as described above, and the cyclo-decelerator is built in the driving motor to decelerate such that the power can be directly transmitted to the wheels. Thus, in the cyclo-decelerating mechanism in which the surfaces of the gears are rubbed against or engaged with each other, since there is no gear sound of meshing the gears, the apparatus can be quietly transferred inside the hospital.

Further, since the backlash is very small, the control ability of the truck is improved, and positioning thereof at the bed side is facilitated.

Also, since the driving motor, the cyclo-decelerator, and the wheel are structured on one axis to be integral such that the wheel is directly driven, the wheel driving section can be structured to be compact.

While the invention has been explained with reference to the specific embodiment of the invention, the explanation is illustrative and the invention is limited only by the appended claims.

What is claimed is:

1. A mobile X-ray apparatus, comprising:

a main frame, a pair of driving motors attached to the main frame and having rotating shafts, a pair of cyclo-decelerating mechanisms respectively fixed to the driving motors, each cyclo-decelerating mechanism including an output shaft, an input shaft attached to the rotating shaft of the driving motor, an eccentric cam attached to the input shaft, a planetary gear with an epitrochoid shape fitted around the eccentric cam and having holes, a disc attached to the output shaft and having a plurality of rollers engaging the holes, and a stationary circular plate having a plurality of stationary pin gears fixed thereto so that when the input shaft is rotated, a peripheral surface of the planetary gear engages the plurality of the stationary pin gears to perform a planetary movement, which is transferred to the disk through the rollers engaging the holes of the planetary gear in a direction opposite to a rotation of the input shaft so that a rotational speed of the driving motor is decelerated and transmitted to the output shaft, and a pair of driving wheels respectively attached to output shafts of the cyclo-decelerating mechanisms, said pair of the driving wheels being individually driven by the respective motors through the respective cyclo-decelerating mechanisms in response to an operation power applied to an operation handle.

2. A mobile X-ray apparatus according to claim 1, further comprising an electromagnetic brake and an encoder, both being attached around the rotating shaft of the driving motor.

* * * * *